United States Patent [19]

Farbood et al.

[11] Patent Number: 5,212,078
[45] Date of Patent: *May 18, 1993

[54] PROCESS FOR PRODUCING A LACTONE

[75] Inventors: Mohamad I. Farbood, Holmdel; James A. Morris, Howell; Arthur E. Downey, Linden, all of N.J.

[73] Assignee: International Flavors and Fragrances Inc., New York, N.Y.

[*] Notice: The portion of the term of this patent subsequent to Nov. 13, 2007 has been disclaimed.

[21] Appl. No.: 513,789

[22] Filed: Apr. 25, 1990

Related U.S. Application Data

[63] Continuation-in-part of Ser. No. 399,826, Aug. 28, 1989, Pat. No. 4,970,163.

[51] Int. Cl.$^5$ .................... C12P 17/04; C12P 17/02; C12P 7/00; C12N 1/16
[52] U.S. Cl. .................... 435/126; 435/123; 435/127; 435/255; 435/132; 435/144; 435/156; 435/911; 549/299
[58] Field of Search ............ 435/255, 123, 127, 126, 435/156, 911, 132, 148, 144, 171; 549/254, 299

[56] References Cited

U.S. PATENT DOCUMENTS 3,905,868  9/1975  Hamsher ........................... 435/44
4,798,799  1/1989  Farbood ........................... 435/254
4,970,163 11/1990  Farbood ........................... 435/255

OTHER PUBLICATIONS de Hoog, Antonie van Leeuwenhoek, 52, (1986), pp. 39–44.
Kockora Kratochrilora, et al, Ceska Mykol, vol. 38 (1), 1984, pp. 11–20.

Primary Examiner—Irene Marx

[57] ABSTRACT

Described is a microbiological method for producing the lactone, sclareolide having the structure:

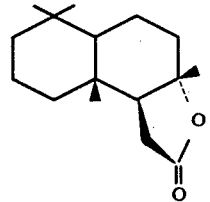

and a diol having the chemical structure:

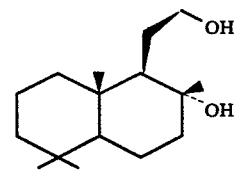

using a sclareol derivative having one of the structures:

(Abstract continued on next page.)

-continued
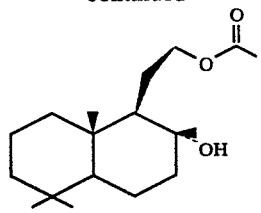
-continued
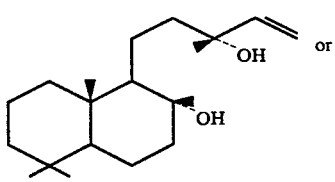 or
wherein a combination of two or more of the compounds as a substrate and using one of the microorganisms:
*Cryptococcus albidus*, ATCC 20918;
*Bensingtonia ciliata*, ATCC 20919;
Cryptoccus laurentii, ATCC 20920; or
Cryptococcus albidus, ATCC 20921.
7 Claims, 4 Drawing Sheets

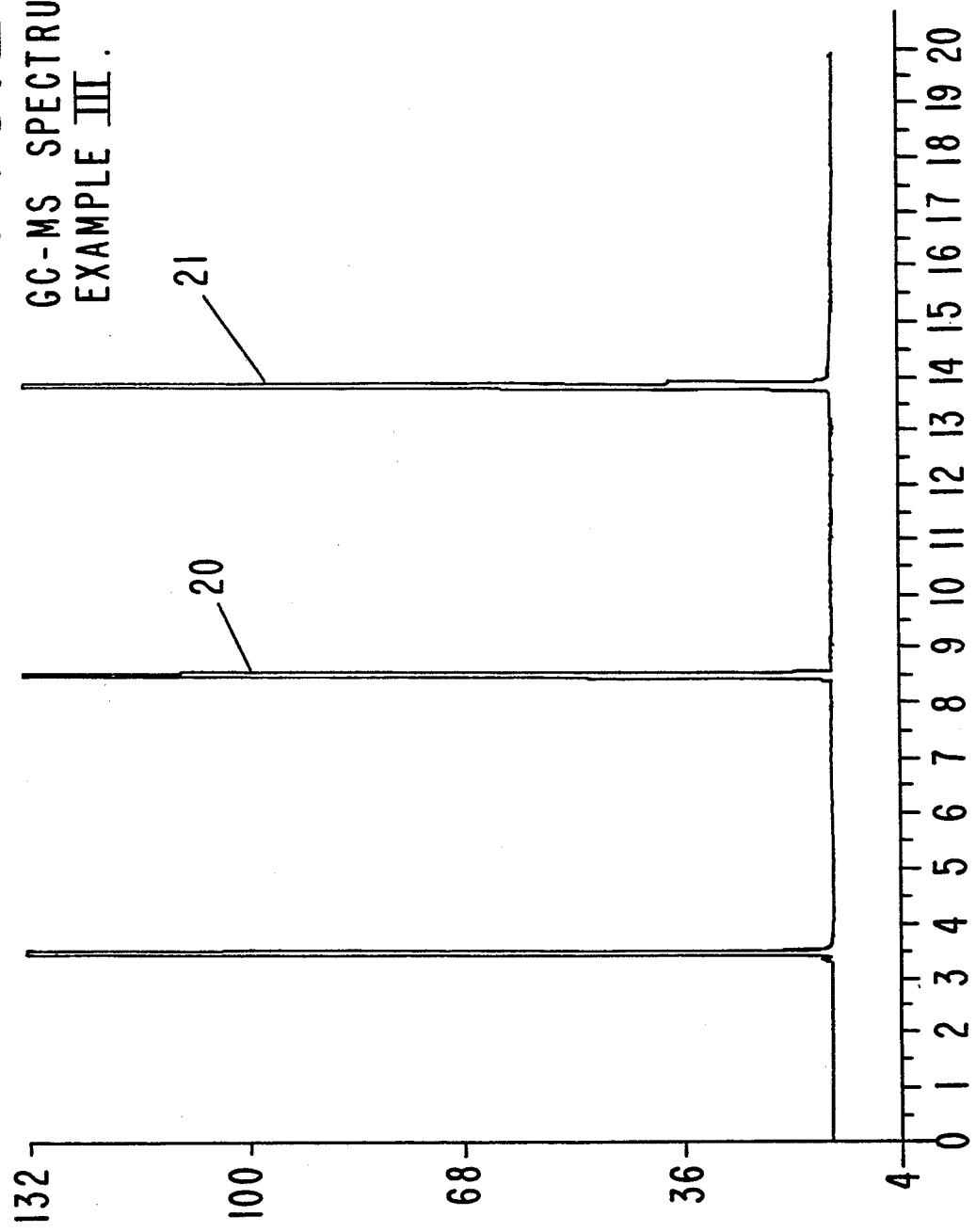

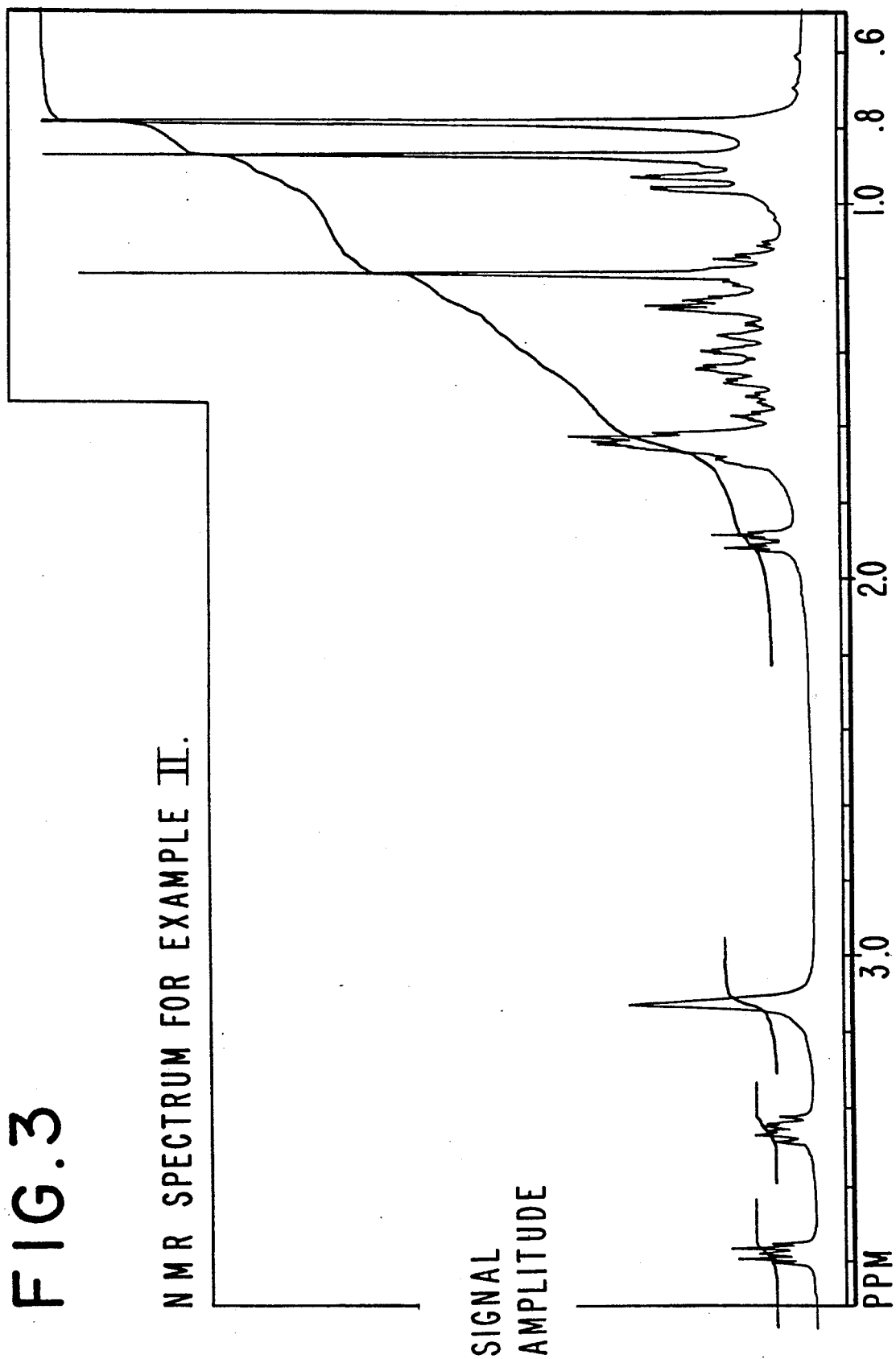
FIG. 3 NMR SPECTRUM FOR EXAMPLE II.

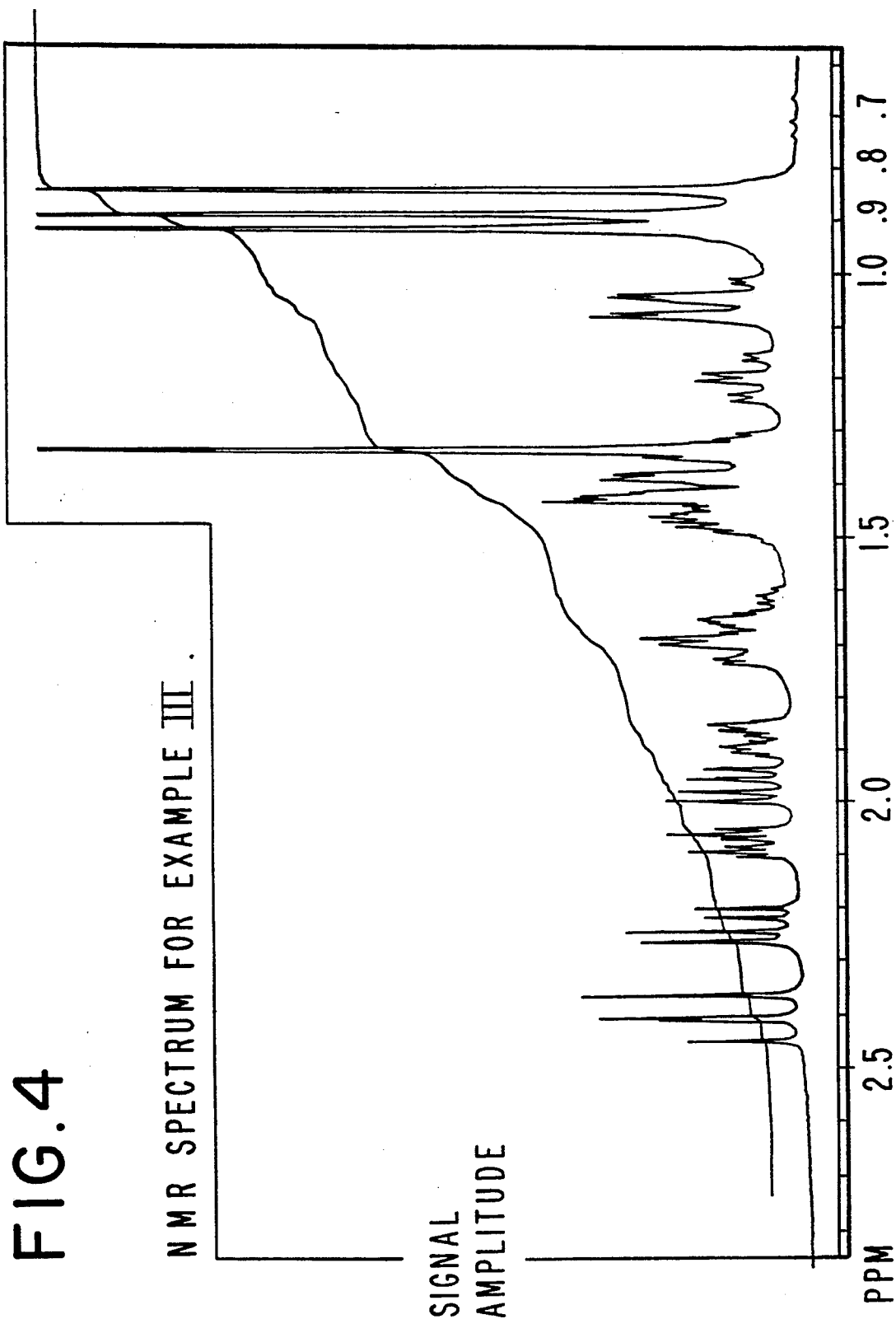

5,212,078

PROCESS FOR PRODUCING A LACTONE

PRIOR RELEVANT APPLICATIONS

This application is a continuation-in-part of application for U.S. Letters Patent, Serial No. 399,826 filed on Aug. 28, 1989 now U.S. Pat. No. 4,970,163 issued on Nov. 13, 1990.

BACKGROUND OF THE INVENTION

The compound sclareolide having the structure:

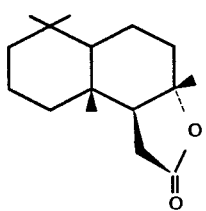

has been found to be a valuable intermediate in preparing the compound having the structure:

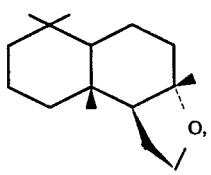

an important material for use in perfumery.

The compound having the structure:

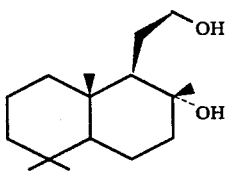

has been shown to be useful in U.S. Pat. No. 4,798,799 issued Jan. 17, 1989 as an intermediate in the creation of the compound having the structure:

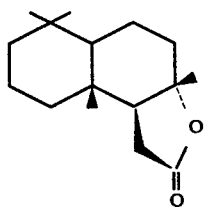

and has also been shown to be a useful precursor of the compound having the structure:

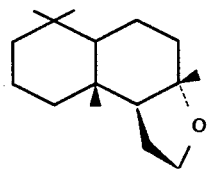

at column 8, lines 58–60 of U.S. Letters Patent 4,798,799.

Indeed, U.S. Letters Patent, 4,798,799 discloses the utilization of a culture containing the microorganism Hyphozyma roseoniger having the identifying characteristics of CBS 214.83 and ATCC 20624 capable of producing the diol having the structure:

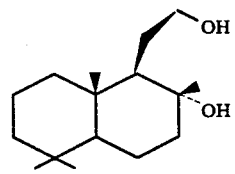

in a recoverable quantity upon the transformation of compounds including the compound having the structure:

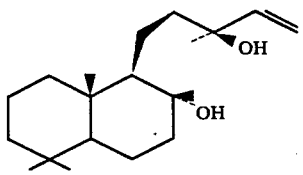

(sclareol). Table IV, thereof at column 12, lines 15-28 discloses yields of 96% when carrying out the reaction:

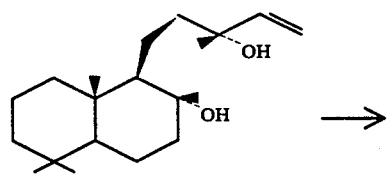 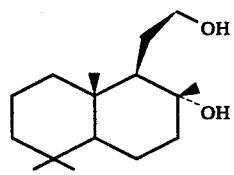

under fermentation conditions using ATCC 20624.

There is no teaching or suggestion in the prior art of either (a) carrying out the reaction:

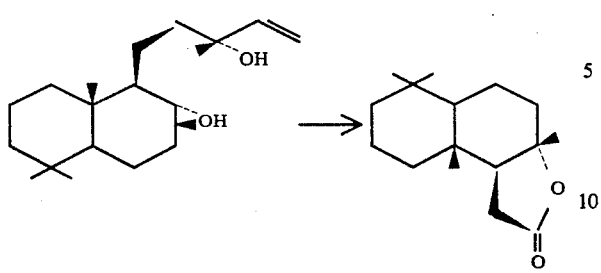

via microbiological methods whereby the compound having the structure:

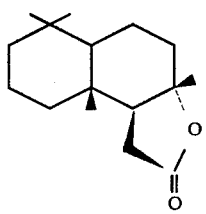

is formed in relatively high yields or (b) carrying out the reaction:

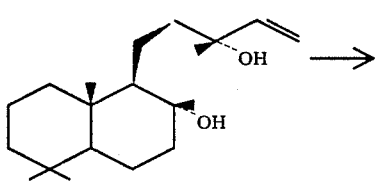

via a microbiological method using the organism *Bensingtonia ciliata*, ATCC 20919 or *Cryptococcus laurentii*, ATCC 20920.

Furthermore, the organisms:

*Cryptococcus albidus*, ATCC 20918;
*Bensingtonia ciliata*, ATCC 20919;
*Cryptococcus laurentii*, ATCC 20920; and
*Cryptococcus albidus*, ATCC 20921 are novel organisms.

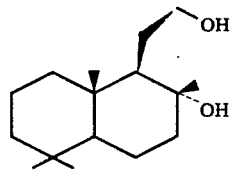

Figure 1:
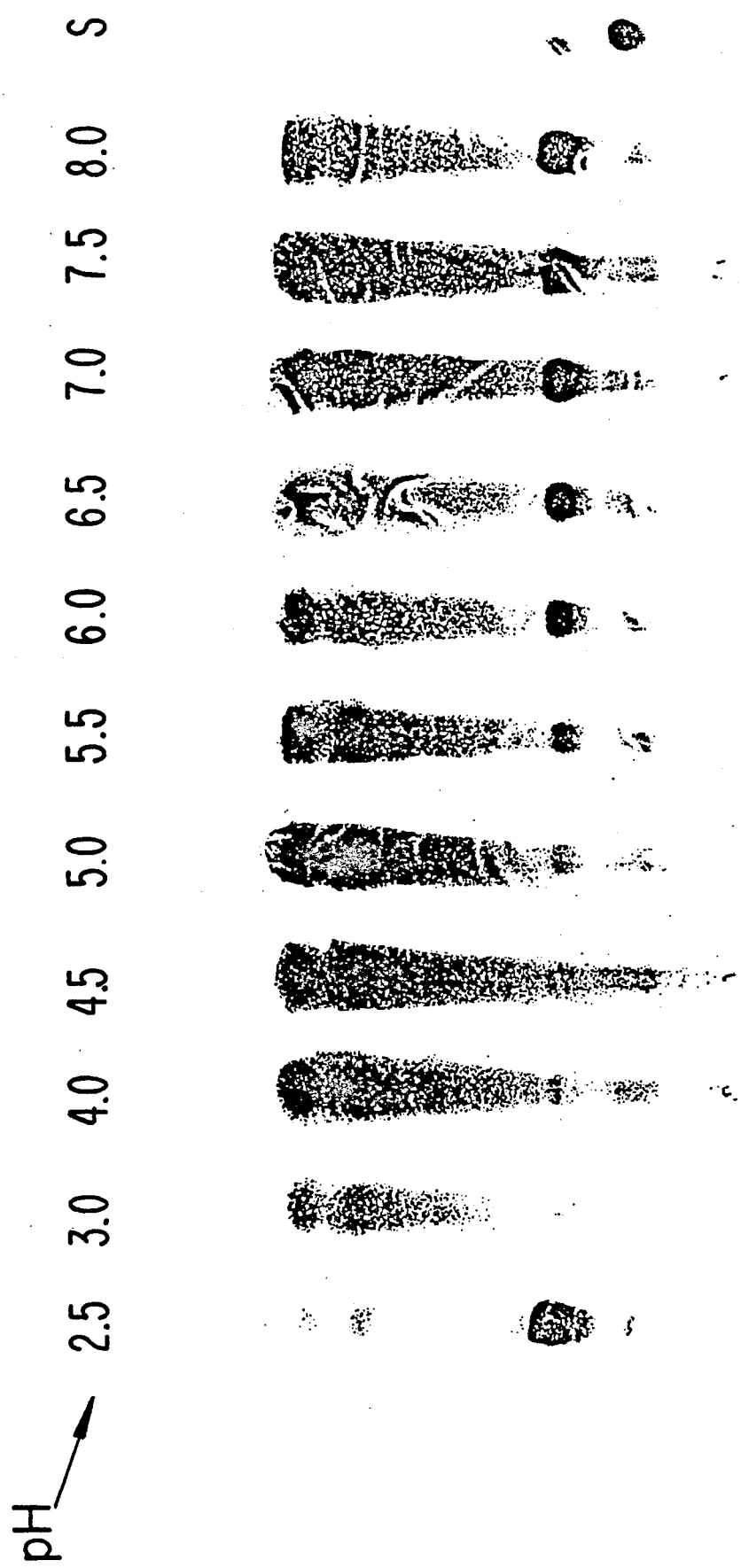
FIG. 1 is a photocopy of the thin layer chromatography eluates of the product of Example I versus pH using *Cryptococcus albidus* (ATCC 20918) whereby sclareolide having the structure.

and the diol intermediate having the structure:

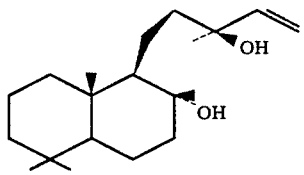

are formed from sclareol having the structure:

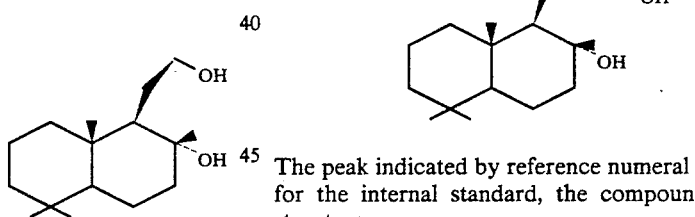

(the substrate).

FIG. 2 is a GC-MS spectrum for the starting material of Example III. The peak indicated by reference numeral 21 is the peak for sclareol having the structure:

The peak indicated by reference numeral 20 is the peak for the internal standard, the compound having the structure:

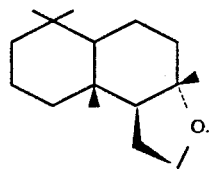

FIG. 3 is the NMR spectrum for the reaction product of Example II, the compound having the structure:

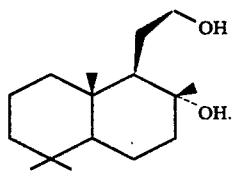

FIG. 4 is the NMR spectrum for the reaction product of Example III having the structure:

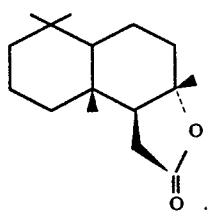

SUMMARY OF THE INVENTION

The present invention concerns biologically pure cultures of the microorganisms:
Cryptococcus albidus, ATCC 20918;
Bensingtonia ciliata, ATCC 20919;
Cryptococcus laurentii, ATCC 20920; and
Cryptococcus albidus, ATCC 20921.

In another embodiment the present invention concerns cultures containing the microorganisms:
Cryptococcus albidus, ATCC 20918;
Bensingtonia ciliata, ATCC 20919;
Cryptococcus laurentii, ATCC 20920; and
Cryptococcus albidus, ATCC 20921,
said cultures individually capable of producing either the diol having the structure:

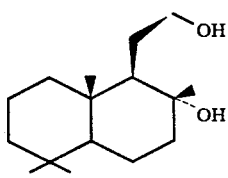

or sclareolide having the structure:

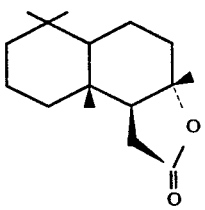

as follows:
Cryptococcus albidus, ATCC 20918 and
Cryptococcus albidus, ATCC 20921,
capable of producing sclareolide having the structure:

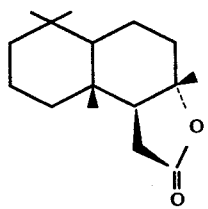

from a mixture of sclareol having the structure:

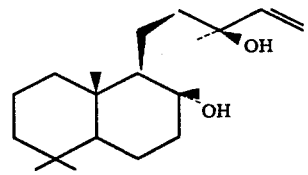

and episclareol having the structure:

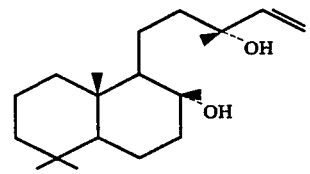

Bensingtonia ciliata, ATCC20919 and Cryptococcus laurentii, ATCC 20920 capable of producing the diol having the structure:

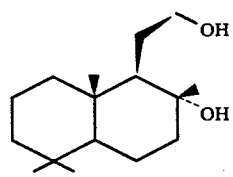

from a mixture of sclareol having the structure:

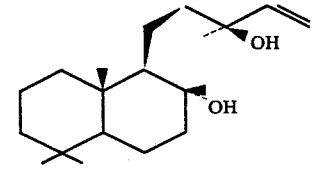

and episclareol having the structure:

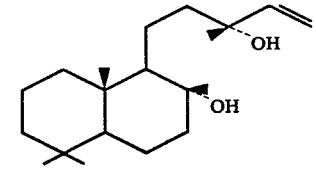

under aerobic conditions in an aqueous nutrient medium.

In still another embodiment the present invention concerns mixtures prepared by cultivating the microorganisms (individually) as follows:
Cryptococcus albidus having the identifying characteristics of ATCC 20918;
Bensingtonia ciliata having the identifying characteristics of ATCC 20919;
Cryptococcus laurentii having the identifying characteristics of ATCC 20920; and
Cryptococcus albidus having the identifying characteristics of ATCC 20921
under aerobic conditions in an aqueous nutrient medium.

In a further embodiment the present invention concerns:

(i) a process for preparing sclareolide having the structure:

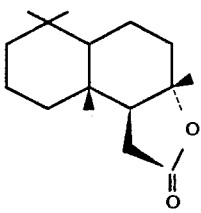

which comprises cultivating either the organism *Cryptococcus albidus* having the identifying characteristics of ATCC 20918 or *Cryptococcus albidus* having the identifying characteristics of ATCC 20921 under aerobic conditions in an aqueous nutrient medium containing one or more of the compounds having the structures:

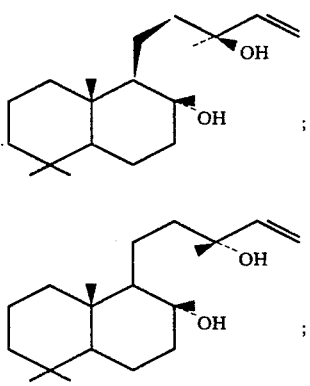

and/or

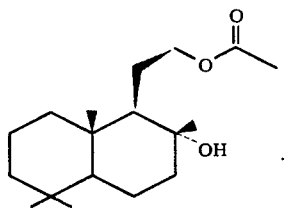

In still a further embodiment the present invention concerns processes for preparing the diol having the structure:

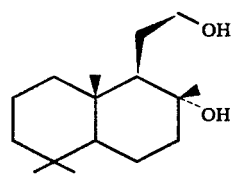

which comprises cultivating either of the microorganisms:

(a) *Bensingtonia ciliata* having the identifying characteristics of ATCC 20919; or
(b) *Cryptococcus laurentii* having the identifying characteristics of ATCC 20920 under aerobic conditions in an aqueous nutrient medium containing one or more of the compounds selected from the group consisting of:

(i) sclareol having the structure:

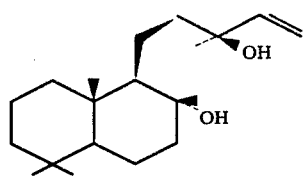

(ii) episclareol having the structure:

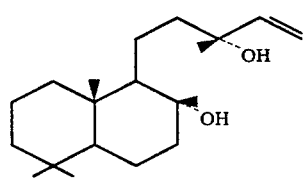

(iii) the acetate having the structure:

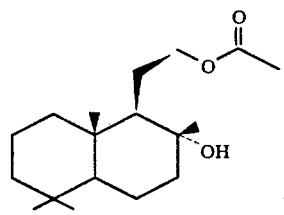

The transformation processes involve cultivation of one of the microorganisms:

*Cryptococcus albidus*, ATCC 20918;
*Bensingtonia ciliata*, ATCC 20919;
*Cryptococcus laurentii*, ATCC 20920; or
*Cryptococcus albidus*, ATCC 20921 in an aqueous nutrient medium in the presence of one, two or all of the compounds having the structures:

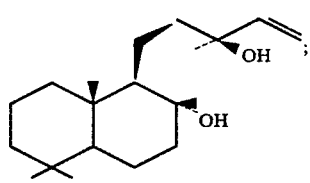

and

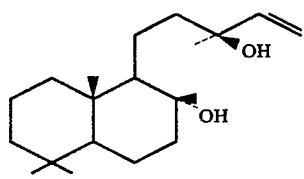

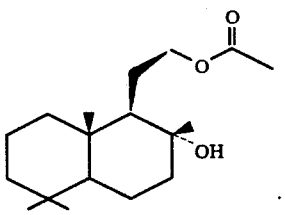

Thus, these compounds may be used singularly or as a mixture containing any number of said compounds.

Thus, in carrying out the reaction using:
*Cryptococcus albidus*, ATCC 20918 or
*Cryptococcus albidus*, ATCC 20921
the following reactions can take place:

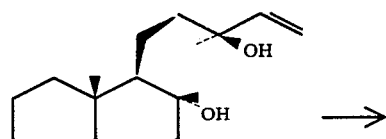

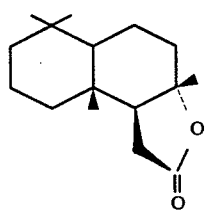

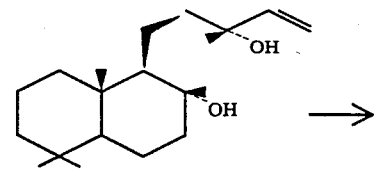

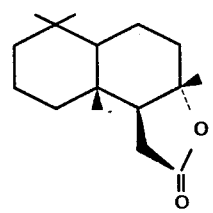

and/or

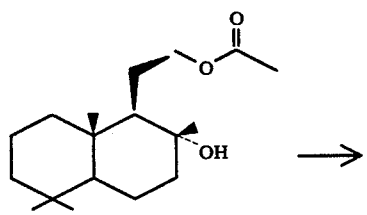

In carrying out the reactions using *Bensingtonia ciliata*, ATCC20919 or *Cryptococcus laurentii*, ATCC 20920 the following reactions can take place:

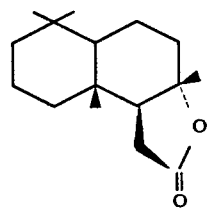

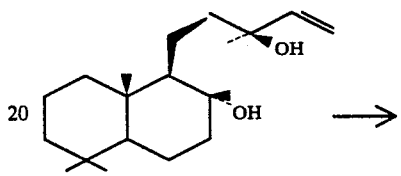

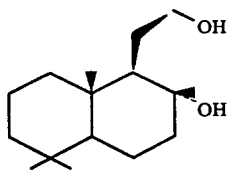

and/or

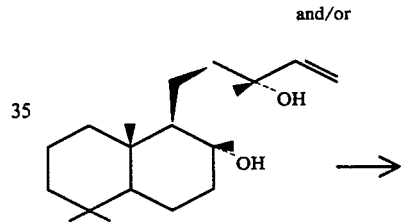

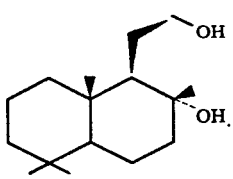

The form in which the microorganisms are used is not critical. They can be used as the culture (suspension), i.e., including the cells and the corresponding nutrient solution, or in the form of cells suspended in a buffer solution. The cells, or an enzyme extract thereof, may be immobilized on a suitable solid support, which may then be used to effect transformations.

The suspended culture mixture is prepared by inoculation of a suitable aqueous nutrient medium with the microorganisms. A suitable nutrient medium is one which contains nitrogen sources, inorganic salts, growth factors, the desired substrate(s), and optionally other carbon sources. Some carbon sources suitable for use in the inventive process include, for example, glucose, galactose, L-sorbose, maltose, sucrose, cellobiose, trehalose, L-arabinose, L-rhamnose, ethanol, glycerol, L-erythrithol, D-mannitol, lactose, melibiose, raffinose, melezitose, starch, D-xylose, D-sorbitol, a-methyl-D-glucoside, lactic acid, citric acid and succinic acid. Suitable nitrogen sources include, for example, nitrogen-containing organic substances such as peptone, meat extract, yeast extract, corn steep liquor, casein, urea, amino acids, or nitrogen-containing inorganic compounds such as nitrates, nitrites and inorganic ammonium salts. Suitable inorganic salts include, for example, phosphates of magnesium, potassium, calcium, or sodium. The above mentioned culture medium nutrients may be supplemented with, for example, one or more vitamins of the B group and/or one or more trace minerals such as Fe, Mo, Cu, Mn, and B, as desired. The vitamins or trace minerals are not necessary when a small amount of yeast extract is added to the medium. Addition of an antibiotic, such as chloroamphenicol or chlorotetracycline, may be desirable when bacterial contamination is a problem.

The cultivation of the microorganism may be carried out as a stationary culture or as a submerged (e.g., shaking culture, fermentor culture) under aerobic conditions. One may suitably work in the pH range of from about 2.5 to about 9.0, and preferably in the range of from about 3.0 to about 7.5 and most preferably between about 3.0 and 6.5. The pH may be regulated by the addition of inorganic or organic acids, such as hydrochloric acid, acetic acid, and oxalic acid, or by the addition of bases, such as sodium hydroxide, and ammonium hydroxide, or by the addition of a buffer, such as phosphate or phthalate. The incubation temperature should suitably be maintained between about 12° C. and about 33° C., with a range between about 15° C. and about 30° C. being more preferred, and a range between about 18° C. and about 28° C. being most preferred.

The process in accordance with this invention may be conveniently carried out by adding one or a mixture of the compounds having the structures:

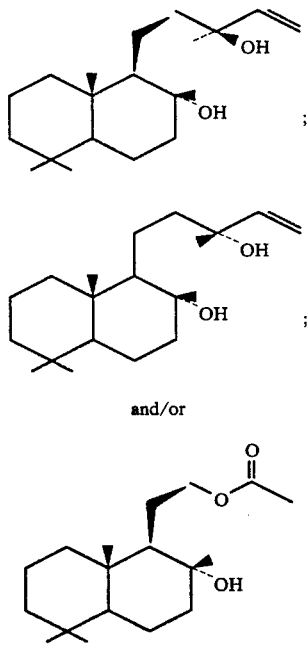

and/or to the nutrient medium at the onset of cultivation, as the sole carbon source. Alternatively, the substrate may be added in combination with another carbon source, such as dextrose, either during cultivation, or when the carbon source is depleted. The only restriction on the concentration of substrate in the culture medium is that of being able to effectively aerate the culture. However, the substrate concentration is preferably in the range of between about 0.1 g/L and about 130 g/L, more preferably in the range of between about 0.5 g/L and about 120 g/L, and most preferably in the range between about 2.5 g/L up to about 100 g/L. The transformation can be suitably carried out under any of the above mentioned conditions.

The total transformation time (after initial cultivation period) may vary depending on the composition of the nutrient medium and the substrate concentration. In general, shaking flask cultures require from between about 12 hours and about 264 hours. However, when a fermentor is used the cultivation time may be reduced to about 48 hours or less.

The transformation may be carried out using the cells of the microorganism isolated from the culture solution, or with an enzyme extract isolated from the cells in a manner well known to the art. In this case, the transformation can be conveniently carried out in a variety of aqueous nutrient media including, for example, in a buffer solution, in a physiological salt solution, in a fresh nutrient solution, or in water. The isolated cells or enzyme extract may be immobilized on a solid support and the desired transformation effected. Also, transformation of the substrate may be effected by mutants of this organism. Such mutants can be readily obtained by methods well known in the art, for example, by exposing the cells to UV or X-rays, or known mutagenic substances, such as, for example, acridine orange.

The substrate can be added to the medium as a powder, or a slurry in an emulsifier such as TWEEN ®80 (polyoxy-ethylenesorbitan mono-oleate), or as a solution in an emulsifier, or as a solution in a hydrophilic solvent such as acetone, methanol, ethanol, ethylene glycol, or dioxan. A surface-active agent, or a dispersion agent can also be added to an aqueous suspension of the substrate, or the substrate can be emulsified using ultrasound.

Conventional antifoam agents, such as silicone oils (e.g., UCON), polyalkyleneglycol derivatives, maize oil, or soya oil, can be used to control foaming.

The transformation of the substrate can be monitored using standard analytical techniques such as GLC, TLC, HPLC, IR and NMR. If a rapid disappearance of the substrate is observed more substrate can then be added, in order to maximize the transformation capacity of the microorganism. The process is generally terminated when most of the substrate has disappeared from the culture medium. Depending upon the microorganism used, the compound having the structure:

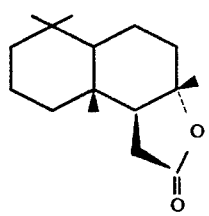

or the compound having the structure:

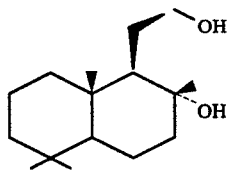

may be recovered from the aqueous nutrient medium. The compound having the structure:

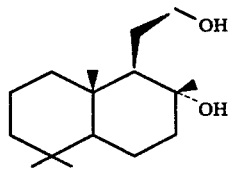

may be cyclized to the compound having the structure:

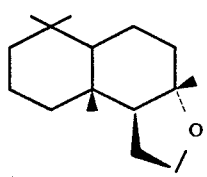

as stated at lines 52 and 53, at column 8 of U.S. Pat. No. 4,798,799 the specification for which is incorporated by reference herein. The compound having the structure:

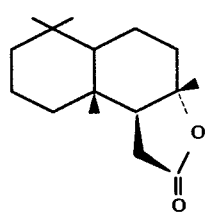

may also be used as is for its flavor or fragrance value or it may be reduced to the compound having the structure:

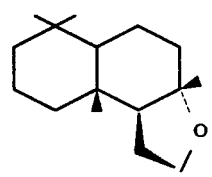

according to the reaction:

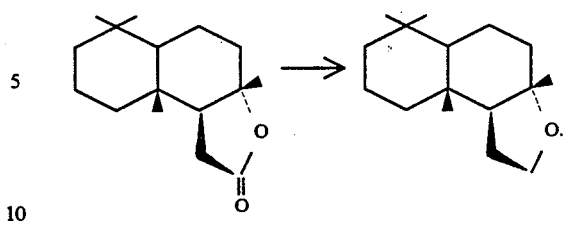

Isolation and purification of the compounds having the structures:

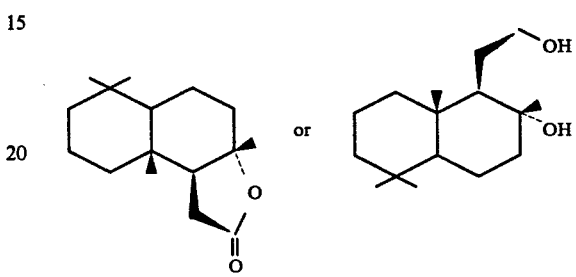

from the fermentation broths may be achieved by conventional techniques including, filtration or centrifugation, solvent extractio, distillation, crystallization, and the like.

The compound having the structure:

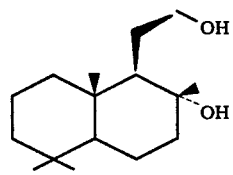

may be converted to the compound having the structure:

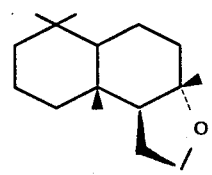

by conventional cyclization methods well known in the art as specified at lines 58-68, at column 8 of U.S. Letters Patent 4,798,799 and at column 9, lines 1 and 2 of U.S. Pat. No. 4,798,799.

Each of the microorganisms employed in this invention was isolated from a soil sample obtained from various geographical locations. Each of the strains has been deposited with the American Type Culture Collection with the accession numbers as follows:

Cryptococcus albidus, ATCC 20918;
Bensingtonia ciliata, ATCC 20919;
Cryptoccus laurentii, ATCC 20920; and
Cryptococcus albidus, ATCC 20921.

The organisms Bensingtonia ciliata and Cryptococcus laurentii were also studied by Centralbureau voor Schimmel Cultures (CBS). CBS assigned both of these organisms the name: *Lecythophere hoffmannii* (van Beijma), *W. Gams* (synonym *Phialophora hoffmannii*) because this is a filamentous fungus according to CBS.

The organism *Cryptococcus albidus*, ATCC 20918 was also studied by Centraalbureau voor Schimmelkultur (CBS). CBS named this culture to be *Cryptococcus albidus* var. albidus (Saito) Skinner.

The organism *Cryptococcus albidus*, ATCC 20918 is described as follows:

---

Morphology: Growth in liquid medium showed unipolar budding cells. A film stayed on the surface of the liquid while heavy sediment was observed. Growth on solid agar was unicellular with colonies being white to slightly pinkish, very shiny, bright, slimy, round and with smooth borders. No pseudohyphae were formed on corn meal aga.

| Physiology and Biochemistry: | | | |
|---|---|---|---|
| Carbon Assimilation: (Growth) | | Carbon Assimilation: (Growth) | |
| Glucose | + | D-ribose | U |
| Galactose | + | L-rhamnose | + |
| L-sorbose | + | D-glucosamine | + |
| Maltose | + | Ethanol | U |
| Sucrose | + | Erythritol | — |
| Cellobiose | + | Glycerol | U |
| Trehalose | + | Adonitol (Ribitol) | + |
| Lactose | + | Dulcitol (Galactitol) | + |
| Melibiose | — | D-mannitol | + |
| Raffinose | + | D-sorbitol (glucitol) | + |
| Melezitose | + | a-methyl-D-glucoside | + |
| Inulin | — | Salicin | + |
| Soluble Starch | — | Inositol | + |
| D-xylose | — | Lactic acid | — |
| L-arabinose | — | Citric acid | — |
| D-arabinose | — | | |
| Succinic acid | + | | |
| Growth at 30° C. | + | | |
| Growth at 37° C. | — | | |
| Vitamin free growth | — | | |
| Splitting of arbutin | + | | |
| Nitrogen assimilation: | | | |
| NH₄NO₃ | + | | |
| KNO₃ | + | | |
| NO₂ | + | | |
| Ethylamine | + | | |
| Fermentation (Acid from): | | | |
| Glucose | — | | |
| Galactose | — | | |
| Maltose | — | | |
| Sucrose | — | | |
| Lactose | — | | |
| Raffinose | — | | |
| Melibiose | — | | |
| Inulin | — | | |
| Cellobiose | — | | |
| Melezitose | — | | |
| Starch | — | | |
| Trehalose | — | | |

Note: U = undecided or questionable

---

The organism *Bensingtonia ciliata*, ATCC 20919 is described as follows:

---

Morphology: On Yeast Maintenance Broth (ATCC medium #200) cells are globose with 1-3 buds per cell. On solid medium cells become filamentous with ballistospores produced. Colonies are tan-salmon in color, flat, dull, with smooth edges. On Corn Meal Agar (ATCC medium #307) true mycelium was noticed after 3 weeks.

| Physiology: | | | |
|---|---|---|---|
| Carbon Assimilation: | | Carbon Assimilation: | |
| Glucose | + | D-ribose | — |
| Galactose | + | L-rhamnose | + |
| L-sorbose | + | D-glucosamine | + |
| Maltose | + | Ethanol | W |
| Sucrose | + | Erythritol | + |
| Cellobiose | + | Glycerol | + |
| Trehalose | + | Adonitol (Ribitol) | W |
| Lactose | — | Dulcitol (Galactitol) | W |
| Melibiose | + | D-mannitol | W |
| Raffinose | + | D-sorbitol (glucitol) | W |
| Melezitose | + | a-methyl-D-glucoside | W |
| Inulin | — | Salicin | W |
| Soluble Starch | + | Inositol | — |
| D-xylose | + | Lactic acid | — |
| L-arabinose | + | Citric acid | — |
| D-arabinose | — | Succinic acid | W |
| Vitamin free growth | — | | |
| Nitrogen assimilation: | | | |
| NH₄NO₃ | W | | |
| Growth at elevated temp: | | | |
| 30° C. | W/— | | |
| 37° C. | — | | |
| Taxonomic Description: | | | |
| *Bensingtonia ciliata* C.T. Ingold | | | |
| Hyphomycete (*Fungi Imperfecti*) | | | |

Note: W = weak

---

A ballistosporic fungus (Spores forcibly abjected).

The ballistospores are colorless, ovoid, 2×5μ, mostly 8×5μ in liquid culture, pointed at the apex and with a flatteneu base.

The ballistospores germinate with the formation of yeast-like blastospores that upon repeated spore formation result in typical yeast colonies (see photo).

Some ballistospores germinate with the formation of short hyphae that produce ballistospores and with repeated spore discharge result in colonies entirely of the hyphae type (see photo).

Evaluation from the following media:

| ATCC medium | |
|---|---|
| #307 | Corn Meal Agar (Difco 0386) and ½ strength Corn Meal Agar |
| #200 | Yeast Malt Agar (Difco 0712) |
| #331 | Neuropora Agar (Difco 0321) |
| #1245 | YEPD |
| #324 | Malt Extract Agar (Difco 0024) |
| #336 | Potato Dextrose Agar |
| #343 | V-8 Juice Agar |

References:
1. Ingold, C.T. (1986) *Bensingtonia ciliata* Gen. et. sp. nov., Ballistoporic Fungus. Trans. Br. Mycol. Soc. 86(2): 325-328.
2. Ingold. C.T. (1988) Further Observations on *Bensingtonia ciliata*. Trans. Br. Mycol. Soc. 91(1): 162-166.

| Physiology and Biochemistry: | | | |
|---|---|---|---|
| Carbon Assimilation: (Growth) | | | |
| Glucose | + | D-ribose | + weak |
| Galactose | + | L-rhamnose | + |
| L-sorbose | + weak | D-glucosamine | V |
| Maltose | + | Ethanol | + |
| Sucrose | + | Erythritol | + |
| Cellobiose | + | Glycerol | + |
| Trehalose | + | Adonitol (Ribitol) | + weak |
| Lactose | + weak | Dulcitol (Galactitol) | V |
| Melibiose | + | D-mannitol | + |
| Raffinose | + | D-sorbitol (glucitol) | + |
| Melezitose | + | a-methyl-D- | + |

-continued

| | | glucoside | |
|---|---|---|---|
| Inulin | + | Salicin | + |
| Soluble Starch | + | Inositol | + |
| D-xylose | + | Lactic acid | + |
| L-arabinose | + | Citric acid | + |
| D-arabinose | + weak | Succinic acid | + |
| Nitrogen Assimilation: | | | |
| $NH_4NO_3$ | + | | |
| $KNO_3$ | + | | |
| $NO_2$ | + | | |
| Ethylamine | + | | |
| Vitamin free growth | + | | |
| Splitting of arbutin | + | | |
| Fermentation (Gas Production): | | | |
| Glucose | − | | |
| Galactose | − | | |
| Maltose | − | | |
| Sucrose | − | | |
| Lactose | − | | |
| Raffinose | − | | |
| Melibiose | − | | |
| Inulin | − | | |
| Cellobiose | − | | |
| Melezitose | − | | |
| Starch | − | | |
| Trehalose | − | | |

Morphology: Pink slimy colonies; round budding cells, heavy sediment in flask; on Dalmau plate thin hyphae were formed.
Reference: C. P. Kurtzman, Mycologia 65; p. 388-395, 1973.
Note: V = variable.

*Cryptococcus albidus*, ATCC 20921 is described as follows:

| Physiology and Biochemistry: | | | |
|---|---|---|---|
| Carbon Assimilation: | | | |
| Carbon Assimilation: (Growth) | | | |
| Glucose | + | D-ribose | − |
| Galactose | + | L-rhamnose | + |
| L-sorbose | + | D-glucosamine | + |
| Maltose | + | Ethanol | V |
| Sucrose | + | Erythritol | − |
| Cellobiose | + | Glycerol | V |
| Trehalose | + | Adonitol (Ribitol) | V |
| Lactose | + | Dulcitol (Galactitol) | + |
| Melibiose | − | D-mannitol | + |
| Raffinose | + | D-sorbitol (glucitol) | + |
| Melezitose | + | a-methyl-D-glucoside | + |
| Inulin | − | Salicin | + |
| Soluble Starch | + | Inositol | + |
| D-xylose | + | Lactic acid | − |
| L-arabinose | + | Citric acid | − |
| D-arabinose | + | Succinic acid | + |
| Nitrogen Assimilation: | | | |
| $NH_4NO_3$ | + | | |
| $KNO_3$ | + | | |
| $NO_2$ | + | | |
| Ethylamine | + | | |
| Vitamin free growth | + | | |
| Splitting of arbutin | + | | |
| Fermentation (Gas Production): | | | |
| Glucose | − | | |
| Galactose | − | | |
| Maltose | − | | |
| Sucrose | − | | |
| Lactose | − | | |
| Raffinose | − | | |
| Melibiose | − | | |
| Inulin | − | | |
| Cellobiose | − | | |
| Melezitose | − | | |
| Starch | − | | |

-continued

| | |
|---|---|
| Trehalose | − |

Morphology: Yellowish-tan, slimy colonies; round budding cells; heavy sediment in the flask, no pseudomycelium or true mycelium.
Note: V = variable.

The following examples serve to illustrate embodiments of the invention as it is now preferred to be practiced but in no way are said Examples meant to limit the scope thereof. Unless otherwise stated weights are in grams, temperatures are in degrees centigrade and pressure is in mm/Hg..

EXAMPLE I

Effect of pH on Conversion of Sclareol To Sclareolide Using *Cryptococcus Albidus* (Saito [Skinner Var. Albidus])(ATCC 20918)

Reactions:

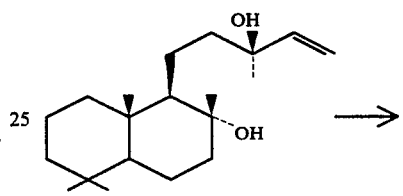
→

and

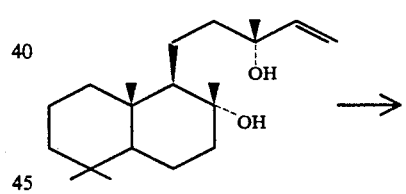
→
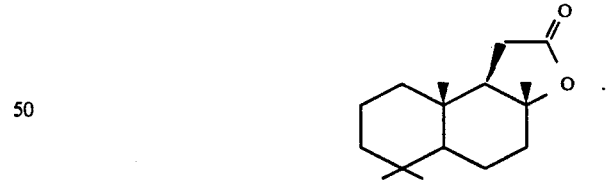

The following medium was prepared:

| | |
|---|---|
| $NH_4NO_3$ | 0.1% |
| $KH_2PO_4$ | 0.1% |
| $MgSO_4.7H_2O$ | 0.05% |
| Yeast Extract | 0.2% |

Eleven 500 ml flasks each containing 100 ml of medium and 1 g of sclareol in TWEEN ®(ratio of sclareol of TWEEN ®80=2:1).

Each flask was inoculated with 5 ml of a 24 hour culture grown on dextrose at 25° C. and 150 rpm. Product and substrate were monitored by TLC against a known standard.

The "substrate" is sclareol which is an 80:20 mixture of the compound having the structure:

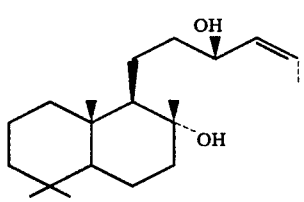

and the compound having the structure:

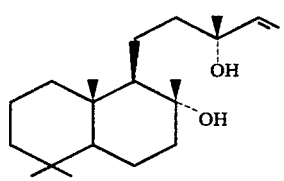

the "Intermediate" is the compound having the structure:

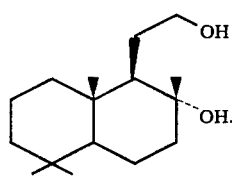

The "product" is sclareolide, the compound having the structure:

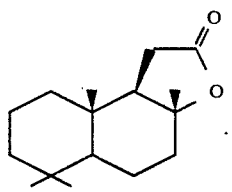

TABLE I

| Flask No. | pH | DURATION | | |
|---|---|---|---|---|
| | | 24 Hours | 48 Hours | 72 Hours |
| 1 | 2.5 | TP + S + TI | P + S + I | P + S + TI |
| 2 | 3.0 | P + TS + I | P + S + I | P |
| 3 | 3.5 | P + TS + TI | P + TI | P |
| 4 | 4.0 | P + TS + I | P + TI | P + TI |
| 5 | 4.5 | P + TS + I | P + I | P + TI |
| 6 | 5.0 | P + TS + I | P + I | P + TI |
| 7 | 7.0 | P + S + I | P + I | P + I |
| 8 | 7.5 | P + S + I | P + I | P + I |
| 9 | 8.0 | P + S + I | P + TI + I | P + I |
| 10 | 8.5 | P + S + I | P + TS + I | P + I |
| 11 | 9.0 | P + S + I | P + TS + I | P + I |

TS: Trace Substrate
S: Sustrate
TP: Trace Product
P: Product
I: Intermediate
TI: Trace Intermediate FIG. 1 sets forth the thin layer chromatographic elutes of product versus pH using *Cryptococcus albidus,* (ATCC 20918).

EXAMPLE II

Preparation of Diol Intermediate

Reactions:

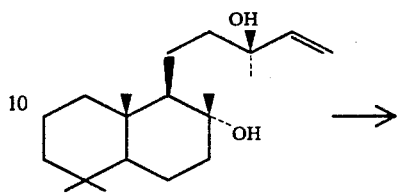

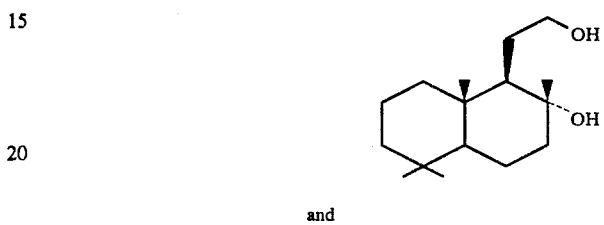

and

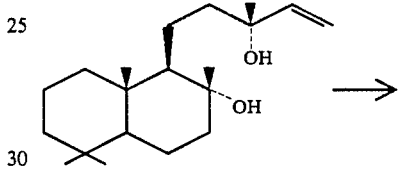

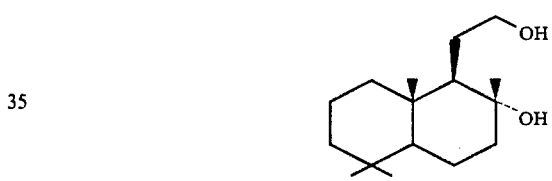

During screening of ten soil samples from Greenwood Forest, Barnegat Township, New Jersey, several flasks showed a spot on the TLC corresponding to the compound having the structure:

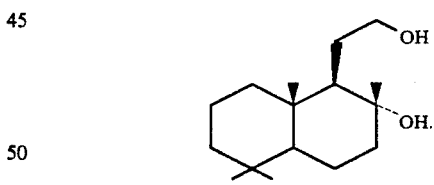

The following medium was prepared:

| $NH_4NO_3$ | 0.2% |
|---|---|
| $KH_2PO_4$ | 0.1% |
| $MgSO_4.7H_2O$ | 0.05% |
| Yeast Extract | 0.2% |
| Dextrose | 1.0%. |

Into a 500 ml flask was placed 100 ml medium and 1.0 g of a 50:50 mixture of sclareol powder:TWEEN ®80. The flask was inoculated with 400 microliters of isolate of *Bensingtonia ciliata,* ATCC 20919 After one week at 25° C. and 150 rpm, the resulting product was extracted with 330 ml of ethyl acetate and the extract dried over anhydrous sodium sulfate. The solvent was removed on a rotary evaporator. The residue was dissolved in hot hexane and ethyl acetate. The resulting extract was permitted to evaporate for a period of 24 hours whereupon were obtained pure crystals (350 mg) of the compound having the structure:

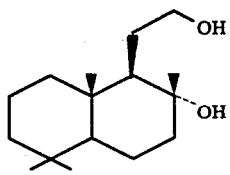

were recovered.

FIG. 3 is the NMR spectrum of the compound having the structure:

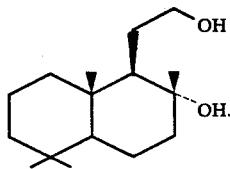

EXAMPLE III

Preparation of Sclareolide Using *Cryptococcus Alibidus* (Saito [Skinner Var. Albidus]), ATCC 20918

Reactions:

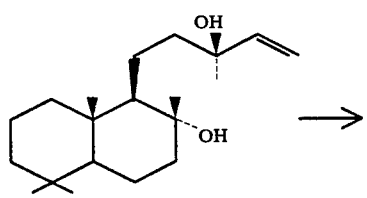

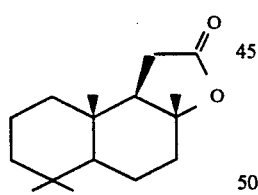

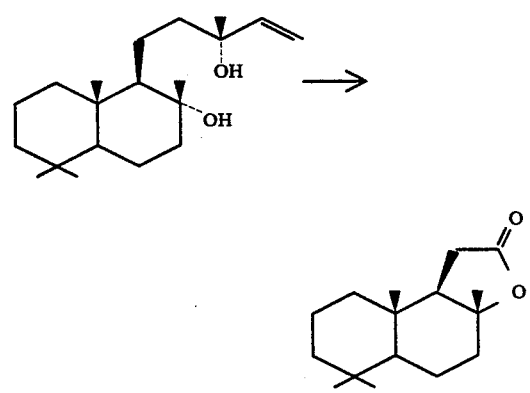

| MEDIUM | | FERMENTER PARAMETERS | |
|---|---|---|---|
| NH₄NO₃ | 0.2% | Temperature: | 25° C. |
| KH₂PO₄ | 0.1% | Aeration: | 1.0 l/min. |
| MgSO₄7H₂O | 0.05% | Agitation: | 430 rpm |
| Yeast Extract | 0.2% | pH = 5.8 controlled with 25% NaOH | |
| Antifoam | 10.0 g | Duration: | 4 days |
| d-H₂O | 8.5 l | | |

SUBSTRATE PREPARATION:

500 Grams of sclareol, 250 grams TWEEN ®80 and 1125 grams of water were placed in a blender and mixed for 5 minutes to form an emulsion.

Fermenter containing above medium was sterilized at 121° C. for 30 minutes and cooled to 25° C. This fermenter was inoculated with 300 ml of 24 hour grown cells of *Cryptococcus albidus* (Saito [Skinner var. albidus]), ATCC 20918. 600 Grams of sclareol emulsion were added at time of inoculation and 600 g portions of emulsion were added at 24, 48, and 72 hours. At 96 hours, the contents of the fermenter were filtered through a 400 mesh sieve. The resulting crude solid product was dissolved in IPA, filtered and the solution concentrated to crystallize; 430 g of pure sclareolide were obtained.

FIG. 2 is a GC-MS spectrum for the initial reaction mass in this Example III. The peak indicated by reference numeral is the peak for the sclareol which is a mixture (80:20) of the compounds having the structures:

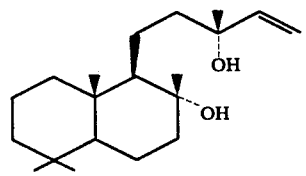

and

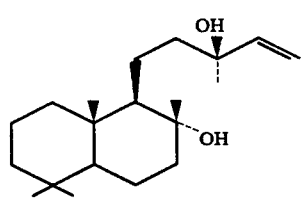

The peak indicated by reference numeral 20 is the peak for the internal standard, the compound having the structure:

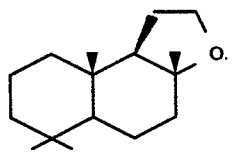

FIG. 4 is the NMR spectrum for the sclareolide produced according to this Example III having the structure:

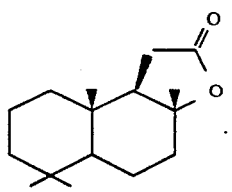

EXAMPLE IV

Production of Sclareolide from Sclareol Using *Cryptococcus Albidus*, ATCC 20918

Same medium and parameters were used as in Example III. The mode of substrate preparation and addition were changed.

One hundred sixty grams of sclareol powder and 80 g of TWEEN ®80 were added to the medium prior to sterilization.

Additional substrate was prepared by mixing finely ground sclareol (2 parts) and TWEEN ®80 (1 part) to form a paste. Two hundred twenty five gram portions of this paste were added at 24, 48, and 72 hours after inoculation.

A total of 655 g of crude sclareolide having a purity of 67.34% was obtained.

EXAMPLE V

Preparation of Sclareolide From Sclareol Using *Cryptococcus Albidus*, ATCC 20921

The same medium and parameters were used as in Example IV. The amount of substrate and agitation were changed.

One hundred fifty grams of sclareol and 75 grams of TWEEN ®80 were added to the medium prior to sterilization.

Only 241 grams of substrate in paste form were after inoculation. Agitation was started at 430 rpm and increased to 630 rpm.

A total of 491 g crude sclareolide having a purity of 44% was obtained, a 94.7% mole/mole conversion.

EXAMPLE VI

Preparation of Sclareolide From Sclareol, Diol Intermediate and Diol Acetate Reactions:

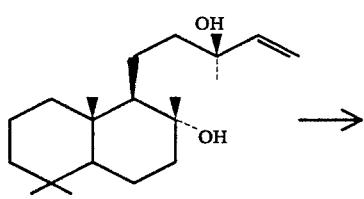

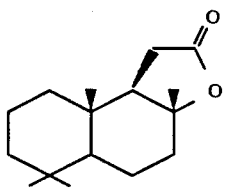

-continued

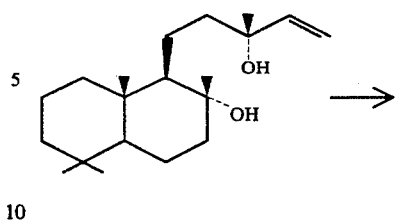

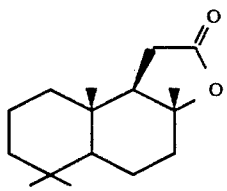

and

The following medium was prepared:

| | |
|---|---|
| NH$_4$NO$_3$ | 0.2% |
| KH$_2$PO$_4$ | 0.1% |
| MgSO$_4$.7H$_2$O | 0.05% |
| Yeast Extract | 0.2% |
| Dextrose | 0.5%. |

A 10 liter fermenter was used with the following operating conditions:
Temperature 25° C.
pH 6.0
Agitation 430 rpm
Sterilization 121° C. for 30 mins.

The fermenter was inoculated with 100 ml of a 48 hour shake flask culture grown on the same medium at 25° C. and 150 rpm.

After 24 hours growth, 200 ml aliquots were removed from the fermenter and centrifuged at 10,000 rpm for 10 minutes in a refrigerated centrifuge. The cells in each tube were washed twice with Butterfield's buffered phosphate.

BUFFER PREPARATION:

| Stock Solution: | |
|---|---|
| Monopotassium hydrogen phosphate | 34.0 g |
| Distilled water | 500.0 ml |

Adjust to pH 7.2 with about 175 ml 1.0N sodium hydroxide solution; dilute to one liter and store.

Diluent Dilute 1.25 ml stock solution to 1 liter with distilled water. Prepare dilution blanks in suitable containers. Sterilize at 121° C. for 15 minutes.

The cells were then taken up in 100 ml of this buffer. The pH was adjusted to 6 and then the material was transferred to a 500 ml flask.

Compounds tested:
a. Sclareol paste in TWEEN ®80 (2:1)=Compound 1.
b. Acetate, compound having the structure:

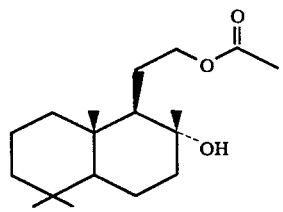

mix in TWEEN ®80 (1:1)=Compound 2.
c. Diol paste, compound having the structure:

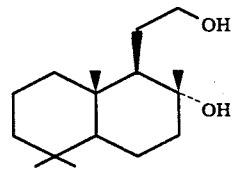

in TWEEN ®80 (1:1)=Compound 3.

300 ml flasks containing 100 ml of buffer and cells (resting cells were placed in shaker incubator at 25° C. and 150 rpm and samples were analyzed using TLC at 24, 48, and 72 hours against the standard known compound. In the following table:

P = Product, sclareolide having the structure:

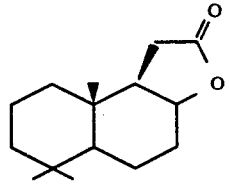

S = Substrate, one of the compounds having the structure:

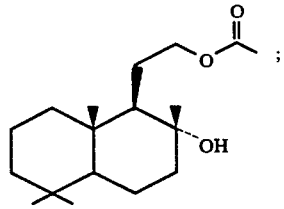

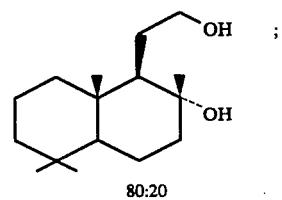

80:20

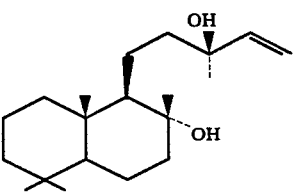

and

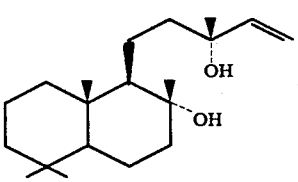

I = Intermediate, compound having the structure:

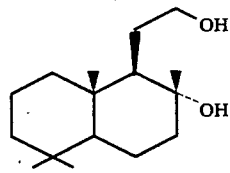

T = Trace.

TABLE II

| Flask | | Duration | | |
|---|---|---|---|---|
| No. | Substrate | 24 Hours | 48 Hours | 72 Hours |
| 1 | 1 g of Compound (1) added | P + S + I | P + I | P + I |
| 2 | 1 g of Compound (2) added | P + TS + I | P + I | P + TI |
| 3 | 1 g of Compound (3) added | TP + S | P + S | P + TS |

EXAMPLE VII

Formation of Diol Intermediate From Sclareol Using *Bensingtonia Ciliata*, ATCC 20919

An experiment using the same procedure as Example II was carried out with the following specifications:

| Organism: *Bensintonia celiata*, ATCC 20919 (IFF-8268C) | | | |
|---|---|---|---|
| MEDIUM | | FERMENTER PARAMETERS | |
| NH₄NO₃ | 40.0 g | Temperature: | 25° C. |
| Yeast Extract | 40.0 g | Aeration: | 2 l/min. |
| KH₂PO₄ | 20.0 g | Agitation: | 300 rpm |
| MgSO₄.7H₂O | 10.0 g | pH = 6.0 controlled with 25% NaOH | |
| Sclareol | 160.0 g | Duration: | 15 days |
| TWEEN ® 80 | 80.0 g | | |
| d-H₂O | 19.0 l | | |

Fermenter containing above medium was sterilized at 121° C. for 30 minutes and cooled at 25° C. This fermenter was inoculated with 1 liter of 48 hour grown culture of *Bensingtonia ciliata*, ATCC 20919. After 15 days of incubation, substrate was converted to product. The contents of the fermenter were filtered through a 400 mesh sieve. The resulting crude solid product was air dried. Total of 101.7 g product was obtained.

What is claimed is:

1. A process for preparing a lactone compound having the structure:

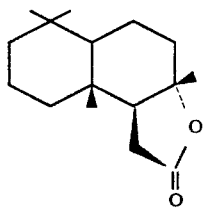

which comprises cultivating a microorganism selected from the group consisting of:

*Cryptococcus albidus*, ATCC 20918; and

*Cryptococcus albidus*, ATCC 20921 to produce said lactone in a recoverable quantity upon the transformation of a substrate comprising a carbon source and in addition, at least one compound selected from the group consisting of:

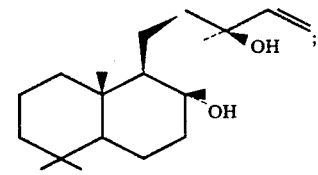

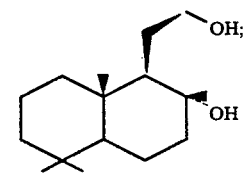

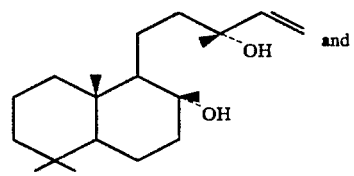

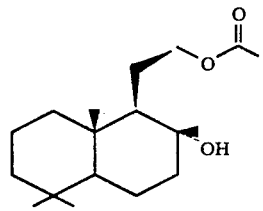

under aerobic conditions in an aqueous nutrient medium containing one or more compounds from said group and an additional carbon source wherein:
  (i) the pH of the reaction mass is between about 2.5 and about 9.0;
  (ii) the temperature of the reaction mass is between about 12° C. and about 33° C.; and
  (iii) the substrate concentration is between about 0.1 grams per liter up to about 130 grams per liter
and recovering said lactone.

2. The process of claim 1 wherein the additional carbon source is dextrose.

3. The process of claim 1 wherein the substrate concentration is between about 0.5 grams per liter and about 120 grams per liter.

4. The process of claim 1 wherein the substrate concentration is between about 2.5 grams per liter and about 100 grams per liter.

5. The process of claim 3 wherein the reaction temperature is between about 15° C. and about 30° C.

6. The process of claim 3 wherein the reaction temperature is between about 18° C. and about 28° C.

7. The process of claim 4 wherein the reaction temperature is between about 18° C. and about 28° C.

* * * * *